United States Patent
Malkowski et al.

(10) Patent No.: US 9,707,011 B2
(45) Date of Patent: Jul. 18, 2017

(54) ATTACHMENTS FOR USE WITH A SURGICAL ACCESS DEVICE

(71) Applicant: Covidien LP, Mansfield, MA (US)

(72) Inventors: Jaroslaw T. Malkowski, Trumbull, CT (US); Kevin Golebieski, Prospect, CT (US); Christopher A. Tokarz, Torrington, CT (US)

(73) Assignee: Covidien LP, Mansfield, MA (US)

( * ) Notice: Subject to any disclaimer, the term of this patent is extended or adjusted under 35 U.S.C. 154(b) by 18 days.

(21) Appl. No.: 14/804,779

(22) Filed: Jul. 21, 2015

(65) Prior Publication Data
US 2016/0128726 A1  May 12, 2016

Related U.S. Application Data

(60) Provisional application No. 62/078,479, filed on Nov. 12, 2014.

(51) Int. Cl.
*A61B 1/32* (2006.01)
*A61B 17/34* (2006.01)
*A61B 17/00* (2006.01)
*A61B 19/02* (2006.01)

(52) U.S. Cl.
CPC ...... *A61B 17/3494* (2013.01); *A61B 17/3423* (2013.01); *A61B 2017/00265* (2013.01); *A61B 2017/3492* (2013.01); *A61B 2019/022* (2013.01); *A61B 2019/0208* (2013.01); *A61B 2019/0239* (2013.01)

(58) Field of Classification Search
CPC ... A61B 17/0218; A61B 17/3423; A61B 1/32; A61B 17/02; A61B 17/0293; A61B 17/3421; A61B 2017/3445; A61B 17/3462

USPC .................................................. 600/201–241
See application file for complete search history.

(56) References Cited

U.S. PATENT DOCUMENTS 2,468,985 A   5/1949   Krotz
3,402,710 A   9/1968   Paleschuck
3,495,586 A   2/1970   Regenbogen
(Continued)

FOREIGN PATENT DOCUMENTS

CA   2702419 A1   11/2010
EP   0226026 A2   6/1987
(Continued)

OTHER PUBLICATIONS

Extended European Search Report corresponding to counterpart Int'l Appln. No. EP 15 19 4026.9, dated Mar. 10, 2016.
(Continued)

*Primary Examiner* — Eduardo C Robert
*Assistant Examiner* — Tara R Carter

(57) ABSTRACT

A surgical access attachment for use with a surgical access device is disclosed. The surgical access attachment includes a ring and an access portion assembly. The ring is configured to engage a proximal portion of a surgical access device. The access portion assembly includes at least one flexible tab having an engagement structure. The engagement structure is configured to selectively engage the ring. The access portion assembly is configured to retain a seal. The access portion assembly is configured to disengage from the ring in response to a predetermined amount of force exerted on one flexible tab of the at least one flexible tab.

19 Claims, 13 Drawing Sheets

(56) References Cited

U.S. PATENT DOCUMENTS

| | | |
|---|---|---|
| 3,674,007 A | 7/1972 | Freis |
| 4,016,884 A | 4/1977 | Kwan-Gett |
| 4,112,932 A | 9/1978 | Chiulli |
| 4,183,357 A | 1/1980 | Bentley et al. |
| 4,356,826 A | 11/1982 | Kubota |
| 4,402,683 A | 9/1983 | Kopman |
| D276,937 S | 12/1984 | Griggs |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,197,955 A | 3/1993 | Stephens et al. |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,350,364 A | 9/1994 | Stephens et al. |
| 5,360,417 A | 11/1994 | Gravener et al. |
| 5,366,478 A | 11/1994 | Brinkerhoff et al. |
| 5,375,588 A | 12/1994 | Yoon |
| 5,391,156 A | 2/1995 | Hildwein et al. |
| 5,394,863 A | 3/1995 | Sanford et al. |
| 5,395,367 A | 3/1995 | Wilk |
| 5,437,683 A | 8/1995 | Neumann et al. |
| 5,443,453 A | 8/1995 | Walker et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,556,387 A | 9/1996 | Mollenauer et al. |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |

(56) References Cited

U.S. PATENT DOCUMENTS

| | | |
|---|---|---|
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,718,628 B2 | 4/2004 | Munshi |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| D545,967 S | 7/2007 | Joyce et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,898 B2 | 9/2010 | Luciano, Jr. et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,226,553 B2 | 7/2012 | Shelton, IV et al. |
| 8,251,900 B2 | 8/2012 | Ortiz et al. |

(56) References Cited

U.S. PATENT DOCUMENTS

| | | |
|---|---|---|
| 8,257,252 B2 | 9/2012 | Kleyman |
| 8,262,568 B2 | 9/2012 | Albrecht et al. |
| 8,317,690 B2 | 11/2012 | Ransden et al. |
| 8,323,184 B2 | 12/2012 | Spiegal et al. |
| 8,328,761 B2 | 12/2012 | Widenhouse et al. |
| 8,343,047 B2 | 1/2013 | Albrecht et al. |
| 8,353,824 B2 | 1/2013 | Shelton, IV et al. |
| 8,388,526 B2 | 3/2013 | Ewers et al. |
| 8,394,018 B2 | 3/2013 | Piskun |
| 8,414,485 B2 | 4/2013 | Richard et al. |
| 8,465,494 B2 | 6/2013 | Butler et al. |
| 8,480,683 B2 | 7/2013 | Fowler et al. |
| 8,550,992 B2 | 10/2013 | Kleyman |
| 8,574,153 B2 | 11/2013 | Richard |
| 8,602,983 B2 | 12/2013 | Kleyman |
| 8,641,610 B2 | 2/2014 | Okoniewski et al. |
| 8,668,641 B2 | 3/2014 | Smith |
| 8,684,918 B2 | 4/2014 | Stopek |
| 8,696,557 B2 | 4/2014 | Fischvogt |
| 8,727,974 B2 | 5/2014 | Kasvikis |
| 8,764,647 B2 | 7/2014 | Kleyman |
| D712,033 S | 8/2014 | Richard et al. |
| D712,034 S | 8/2014 | Richard et al. |
| 8,795,164 B2 | 8/2014 | Stopek |
| 8,795,289 B2 | 8/2014 | Fowler et al. |
| D736,921 S | 8/2015 | Richard et al. |
| 2001/0037053 A1 | 11/2001 | Bonadio et al. |
| 2002/0055714 A1 | 5/2002 | Rothschild |
| 2003/0014076 A1 | 1/2003 | Mollenauer et al. |
| 2003/0093104 A1 | 5/2003 | Bonner et al. |
| 2003/0212383 A1 | 11/2003 | Cote et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0088241 A1 | 4/2007 | Brustad et al. |
| 2007/0118175 A1 | 5/2007 | Butler et al. |
| 2007/0203398 A1 | 8/2007 | Bonadio et al. |
| 2007/0208312 A1 | 9/2007 | Norton et al. |
| 2007/0270654 A1 | 11/2007 | Pignato et al. |
| 2007/0270882 A1 | 11/2007 | Hjelle et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097332 A1 | 4/2008 | Greenhalgh et al. |
| 2008/0161826 A1 | 7/2008 | Guiraudon |
| 2008/0194973 A1 | 8/2008 | Imam |
| 2008/0249371 A1 | 10/2008 | Beckman et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0299292 A1 | 12/2009 | Renaux |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0261975 A1 | 10/2010 | Huey et al. |
| 2010/0262080 A1* | 10/2010 | Shelton, IV ....... A61B 17/3423 604/164.09 |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2011/0009704 A1 | 1/2011 | Marczyk et al. |
| 2011/0021877 A1 | 1/2011 | Fortier et al. |
| 2011/0028794 A1 | 2/2011 | Widenhouse et al. |
| 2011/0028891 A1 | 2/2011 | Okoniewski |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0071359 A1 | 3/2011 | Bonadio et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0313250 A1 | 12/2011 | Kleyman |
| 2012/0059640 A1 | 3/2012 | Roy et al. |
| 2012/0130177 A1 | 5/2012 | Davis |
| 2012/0130179 A1 | 5/2012 | Rockrohr |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |

(56) References Cited

U.S. PATENT DOCUMENTS

| | | |
|---|---|---|
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0245425 A1 | 9/2012 | Okoniewski |
| 2012/0253134 A1 | 10/2012 | Smith |
| 2013/0150792 A1 | 6/2013 | Alonso et al. |
| 2013/0178708 A1 | 7/2013 | Malkowski et al. |
| 2013/0184646 A1 | 7/2013 | Richard et al. |
| 2013/0225931 A1 | 8/2013 | Cruz et al. |
| 2013/0245373 A1 | 9/2013 | Okoniewski |
| 2013/0253277 A1 | 9/2013 | Smith |
| 2013/0253278 A1 | 9/2013 | Smith |
| 2013/0274559 A1 | 10/2013 | Fowler et al. |
| 2013/0310651 A1 | 11/2013 | Alfieri |
| 2014/0039268 A1 | 2/2014 | Richard |
| 2014/0051933 A1 | 2/2014 | Okoniewski |
| 2014/0121466 A1 | 5/2014 | Okoniewski et al. |
| 2014/0142392 A1 | 5/2014 | Smith |
| 2014/0171745 A1 | 6/2014 | Stopek |
| 2014/0194696 A1 | 7/2014 | Fischvogt |
| 2015/0038796 A1 | 2/2015 | Okoniewski |
| 2015/0038797 A1 | 2/2015 | Furnish |

FOREIGN PATENT DOCUMENTS

| | | |
|---|---|---|
| EP | 0538060 A1 | 4/1993 |
| EP | 630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 2044889 A1 | 4/2009 |
| EP | 2044897 A1 | 4/2009 |
| EP | 2095781 A2 | 9/2009 |
| EP | 2098182 A2 | 9/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2292165 | 3/2011 |
| EP | 2343019 | 7/2011 |
| EP | 2468196 A1 | 6/2012 |
| EP | 2505153 A1 | 10/2012 |
| GB | 2469083 | 4/2009 |
| WO | 84/01512 | 4/1984 |
| WO | 93/14801 | 8/1993 |
| WO | 94/04067 | 3/1994 |
| WO | 96/10963 | 4/1996 |
| WO | 96/36283 | 11/1996 |
| WO | 97/33520 | 9/1997 |
| WO | 97/42889 A1 | 11/1997 |
| WO | 99/16368 | 4/1999 |
| WO | 99/22804 | 5/1999 |
| WO | 99/29250 | 6/1999 |
| WO | 00/32116 | 6/2000 |
| WO | 00/32120 | 6/2000 |
| WO | 01/08581 | 2/2001 |
| WO | 01/49363 | 7/2001 |
| WO | 0149363 A1 | 7/2001 |
| WO | 02/07611 | 1/2002 |
| WO | 03/034908 A2 | 5/2003 |
| WO | 03/071926 | 9/2003 |
| WO | 2004/043275 | 5/2004 |
| WO | 2004/054456 | 7/2004 |
| WO | 2004/075741 A2 | 9/2004 |
| WO | 2004/075930 | 9/2004 |
| WO | 2005/058409 | 6/2005 |
| WO | 2006/019723 | 2/2006 |
| WO | 2006/100658 A2 | 9/2006 |
| WO | 2006/110733 | 10/2006 |
| WO | 2007/018458 | 2/2007 |
| WO | 2007/095703 | 8/2007 |
| WO | 2007/143200 | 12/2007 |
| WO | 2008/015566 A2 | 2/2008 |
| WO | 2008/042005 | 4/2008 |
| WO | 2008/077080 | 6/2008 |
| WO | 2008/093313 | 8/2008 |
| WO | 2008/103151 | 8/2008 |
| WO | 2008/121294 A1 | 10/2008 |
| WO | 2009/036343 | 3/2009 |
| WO | 2010/000047 | 1/2010 |
| WO | 2010/141409 | 12/2010 |
| WO | 2011/062768 A1 | 5/2011 |

OTHER PUBLICATIONS

European Search Report No. 17179046.9 dated Nov. 10, 2014.
U.S. Appl. No. 14/740,353, filed Jun. 16, 2015; Specification and drawings attached (31 pp.).

* cited by examiner

ATTACHMENTS FOR USE WITH A SURGICAL ACCESS DEVICE

CROSS-REFERENCE TO RELATED APPLICATIONS

This application claims the benefit of and priority to U.S. Provisional Patent Application No. 62/078,479, filed Nov. 12, 2014, the entire disclosure of which is incorporated by reference herein.

TECHNICAL FIELD

The present disclosure is directed to various embodiments of attachments for use with surgical access devices. More particularly, the present disclosure includes attachments that are removably secured to a proximal portion of a surgical access device and allow instrumentation and/or a clinician's hand to be inserted therethrough.

SUMMARY

The present disclosure relates to a surgical access attachment for use with a surgical access device. The surgical access attachment includes a ring and an access portion assembly. The ring is configured to engage a proximal portion of a surgical access device. The access portion assembly includes at least one flexible tab having an engagement structure. The engagement structure is configured to selectively engage the ring. The access portion assembly is configured to retain a seal. The access portion assembly is configured to disengage from the ring in response to a predetermined amount of force exerted on one flexible tab of the at least one flexible tab.

In disclosed embodiments, the access portion assembly is configured to disengage from the ring in response to a predetermined amount of proximally-directed force exerted on one flexible tab of the at least one flexible tab.

It is also disclosed that the surgical access attachment includes a lip disposed on the access portion assembly. The lip is configured to selectively engage the ring. It is further disclosed that the at least one flexible tab consists of one flexible tab, and the lip is disposed 180° from the flexible tab. Additionally, it is disclosed that the access portion assembly consists of two features that are configured to removably engage the ring, the two features including the flexible tab and the lip. It is further disclosed that a distal-most portion of the flexible tab is co-planar with a distal-most portion of the lip. It is also disclosed that the ring includes a proximal wall, a distal wall, and an intermediate wall interconnecting the proximal wall and the distal wall. Each of the lip and the flexible tab is configured to engage a distal surface of the proximal wall of the ring.

In disclosed embodiments, the proximal wall of the ring is configured to be positioned proximally of a proximal-most portion of a surgical access device.

In disclosed embodiments, the access portion assembly includes a proximal seal retaining portion and a distal seal retaining portion. It is also disclosed that the at least one flexible tab extends from the proximal seal retaining portion. It is further disclosed that the at least one flexible tab extends from the proximal seal retaining portion, and the lip extends from the distal seal retaining portion. Additionally, it is disclosed that the at least one flexible tab extends from the proximal seal retaining portion, and at least partially through an opening of the distal seal retaining portion. It is disclosed that the opening of the distal seal retaining portion is defined by a C-shaped projection extending radially outward from an outer ring of the distal seal retaining portion. It is further disclosed that the proximal seal retaining portion includes a plurality of fingers, and the distal seal retaining portion includes a plurality of engagement apertures. Each finger of the plurality of fingers is configured to mechanically engage one engagement aperture of the plurality of apertures.

In disclosed embodiments, the access portion assembly is configured to engage and/or disengage the ring in a single-handed manner, for example in a non-rotatably single-handed manner.

BRIEF DESCRIPTION OF THE FIGURES

Various embodiments of the present disclosure are disclosed herein with reference to the drawings, wherein.

DETAILED DESCRIPTION

Particular embodiments of the present disclosure will be described herein with reference to the accompanying figures. As shown in the figures and as described throughout the following description, and as is traditional when referring to relative positioning on an object, the term "proximal" refers to the portion of the device that is closer to the user and the term "distal" refers to the portion of the device that is farther from the user. In the following description, well-known functions or constructions are not described in detail to avoid obscuring the present disclosure in unnecessary detail.

As defined herein, a surgical site includes an incision in a patient or a natural orifice through which a surgical procedure may be performed.

Figure 1:
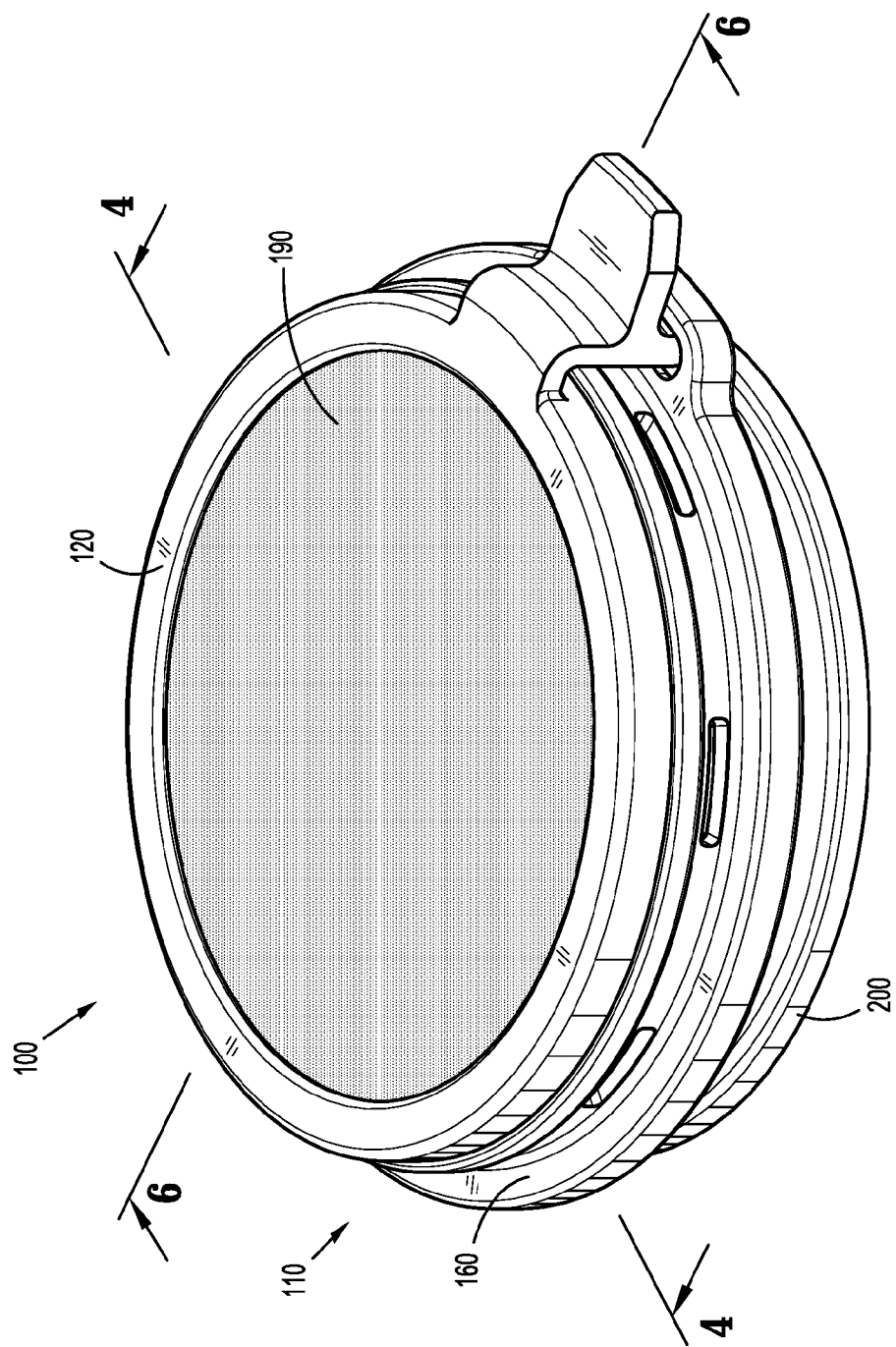
FIG. 1 is a perspective view of a surgical access attachment in accordance with embodiments of the present disclosure.
Figure 2:
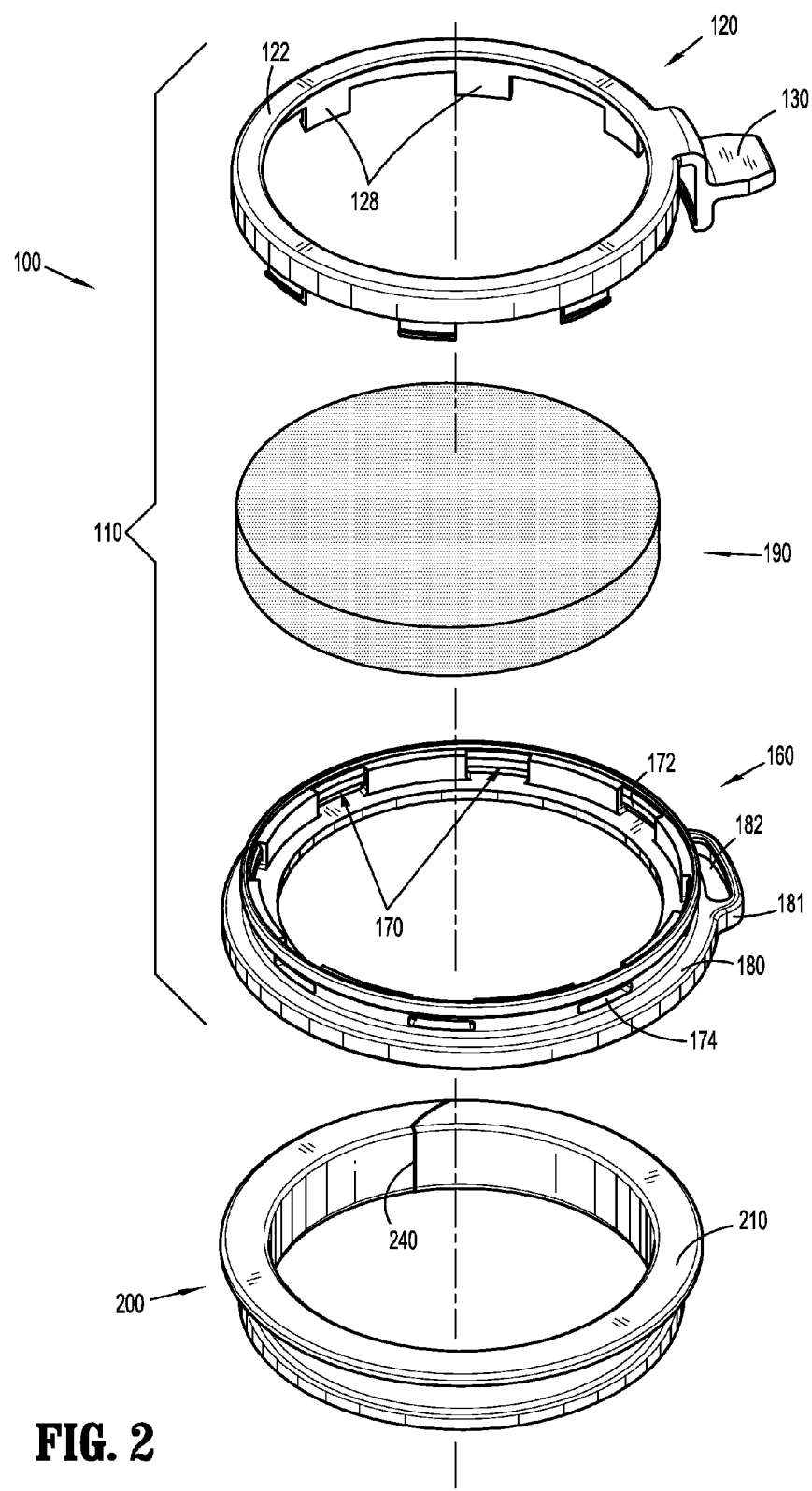
FIG. 2 is an assembly view of the surgical access attachment of FIG. 1 which includes a ring and an access port assembly including a proximal seal retaining portion, a seal, and a distal seal retaining portion.
Figure 7:
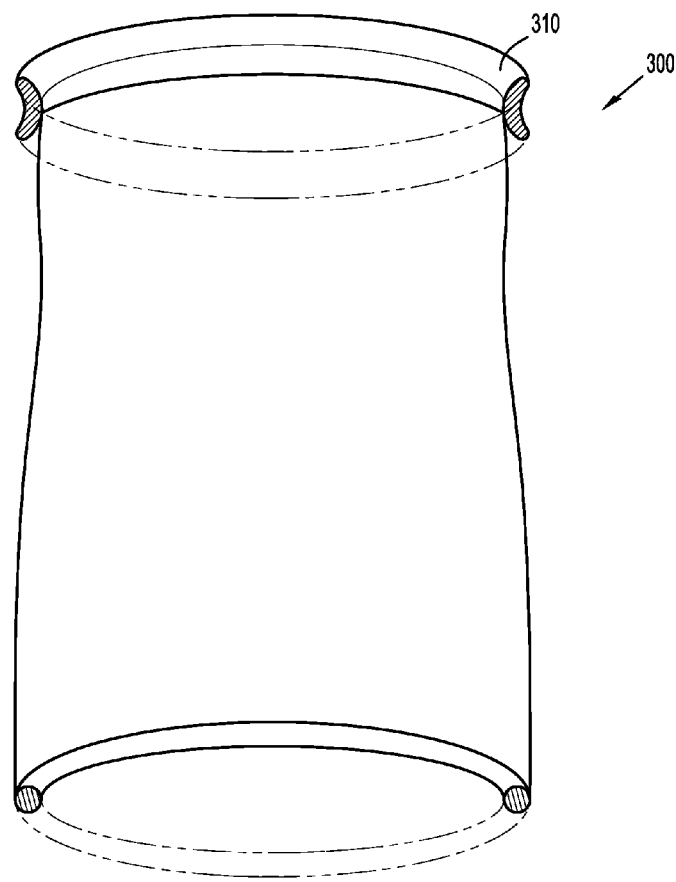
FIG. 7 is a cut-away view of a surgical access assembly for use with a surgical access attachment of the present disclosure.
Figure 8A:
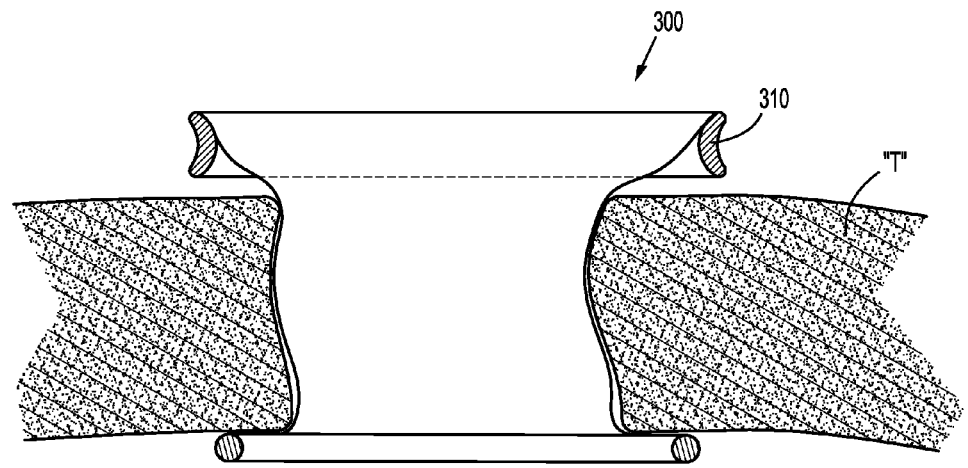
FIG. 8A is a cross-sectional view of the surgical access assembly of FIG. 7 installed in tissue and showing a proximal portion of the surgical access assembly in a concave orientation.

With initial reference to FIGS. 1 and 2, a surgical access attachment 100 is shown in accordance with embodiments of the present disclosure. Surgical access attachment 100 is configured for use with a surgical access device 300 (see FIGS. 7 and 8) for facilitating access through a layer of tissue "T" to a surgical site. More particularly, surgical access attachment 100, or portions thereof, are configured to be selectively removably attached to surgical access device 300, e.g., with the use of a single hand. That is, surgical access attachment 100, or portions thereof, are configured to engage surgical access device 300 in a simple, one-handed manner, and surgical access attachment 100, or portions thereof, are configured to disengage surgical access device 300 in a simple, one-handed manner.

Surgical access attachment 100 includes an access port assembly 110 and a ring 200. Access portion assembly 110 includes a proximal seal retaining portion 120, a distal seal retaining portion 160, and a seal 190. Generally, proximal seal retaining portion 120 and distal seal retaining portion 160 are configured to mechanically engage each other (e.g., via snap-fit engagement) and house seal 190 therebetween. Ring 200 is configured to selectively mechanically engage a proximal portion 310 of surgical access device 300. Access portion assembly 110, which includes proximal seal retaining portion 120, distal seal retaining portion 160 and seal 190, is configured to engage surgical access device 300 by releasably engaging ring 200, which is engaged with surgical access device 300.

Figure 13:
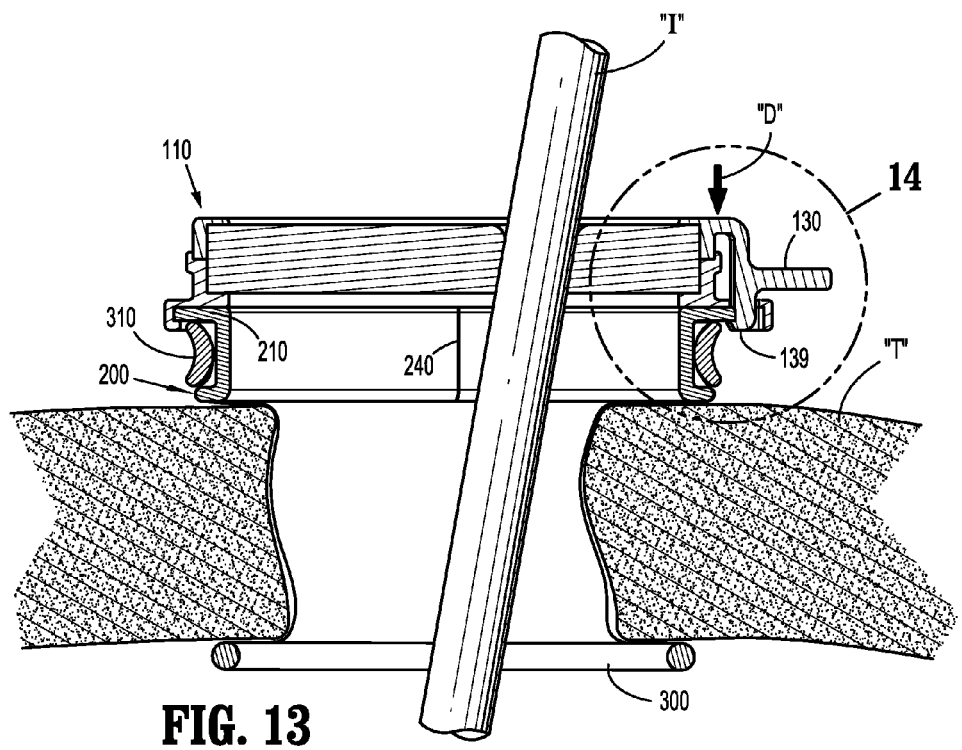
FIG. 13 is a cross-sectional view of the surgical access attachment of FIGS. 1-6 and 9 engaged with the surgical access device of FIGS. 7-8B, and showing instrumentation inserted through the surgical access attachment and the surgical access device.

Seal 190 is configured and dimensioned to fit between proximal seal retaining portion 120 and distal seal retaining portion 160. Seal 190 is configured to allow a surgical instrument "I" (FIG. 13) and/or a clinician's hand to be inserted therethrough in a sealed relationship. As can be appreciated, various types of seals can be used in connection with the present disclosure. Examples of several types of seals are described in commonly-owned U.S. patent application Ser. No. 14/337,430 filed on Jul. 22, 2014, and 62/021,298 filed on Jul. 7, 2014, each of which being incorporated by reference in its entirety herein.

Figure 4:
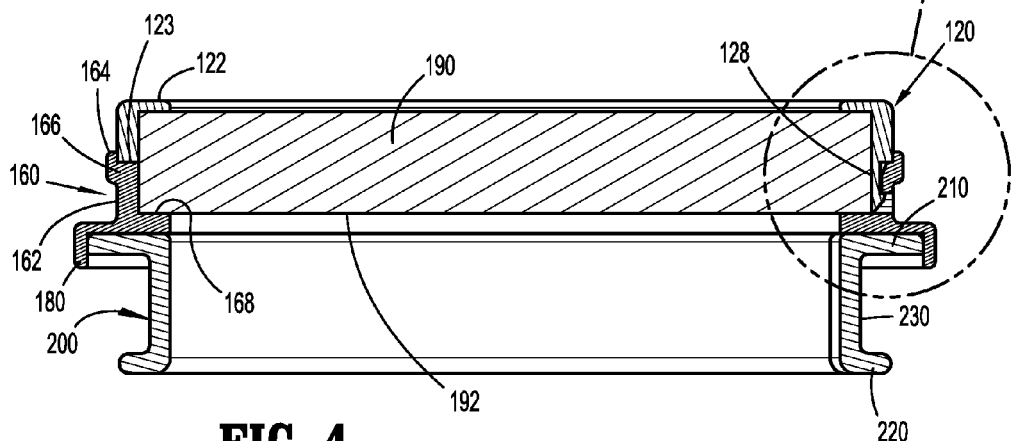
FIG. 4 is a cross-sectional view of the surgical access attachment of FIG. 1 taken along line 4-4 of FIG. 1.
Figure 5:
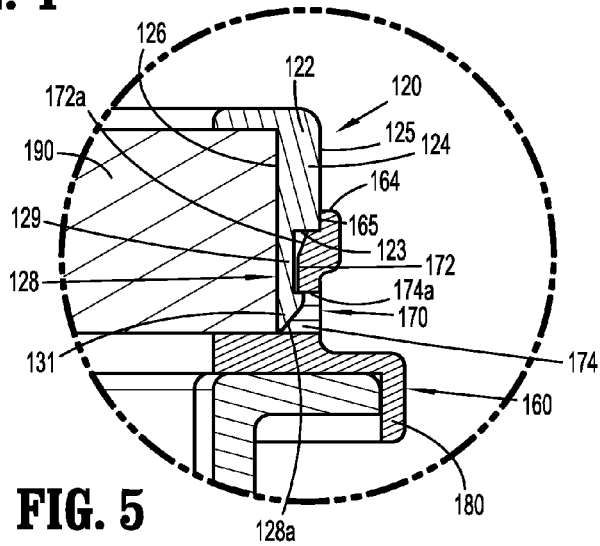
FIG. 5 in an enlarged view of the area of detail indicated in FIG. 4.

With particular reference to FIGS. 2, 4 and 5, proximal seal retaining portion 120 includes a rim 122, a plurality of fingers 128, and a flexible tab 130. Rim 122 includes a generally L-shaped cross-section, a radially outer surface 124, and a radially inner surface 126. Each finger of the plurality of fingers 128 depends distally from a distal surface 123 of rim 122. In the embodiment illustrated in FIGS. 4 and 5, for example, each finger of the plurality of fingers 128 is monolithically formed with rim 122. Additionally, a portion of each finger of the plurality of fingers 128 is configured to mechanically engage a portion of distal seal retaining portion 160, discussed in greater detail below.

Figure 6:
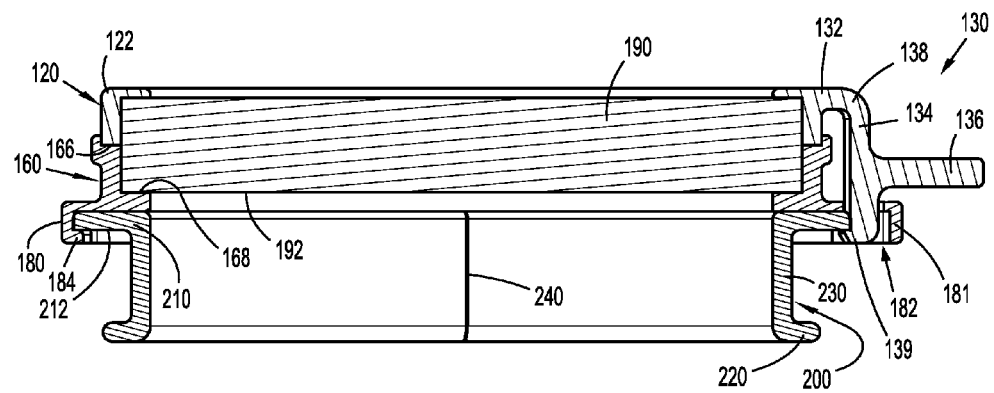
FIG. 6 is a cross-sectional view of the surgical access attachment of FIG. 1 taken along line 6-6 of FIG. 1.

With reference to FIGS. 2 and 6, flexible tab 130 extends radially outward from rim 122, and includes a proximal portion 132, a leg 134, an engagement portion 136, and a living hinge 138. Living hinge 138 interconnects proximal portion 132 and leg 134, and enables leg 134 to flex with respect to proximal portion 132. Engagement portion 136 extends radially outward from leg 134 and is configured for engagement by a user to facilitate the flexing of leg 134 with respect to proximal portion 132. Additionally, leg 134 includes an engagement structure 139 disposed on a distal end thereof, which is configured to mechanically engage a portion of ring 200, discussed in greater detail below.

Figure 3:
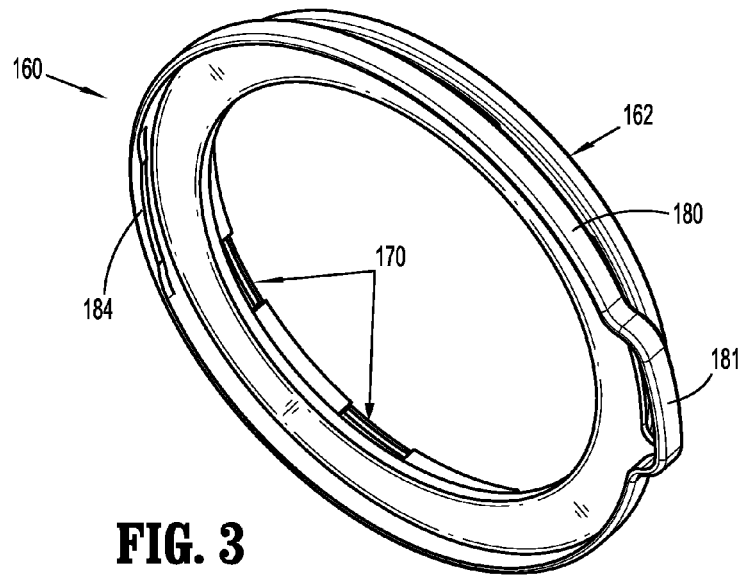
FIG. 3 is a perspective view of the distal seal retaining portion of the access port assembly of FIG. 2.

With reference to FIGS. 2-6, distal seal retaining portion 160 includes a body 162, a proximal edge 164, a proximal shelf 166, a distal shelf 168, a plurality of engagement apertures 170, an outer ring 180, and a lip 184 (see FIGS. 3 and 6). Proximal edge 164 is configured to at least partially radially surround a distal portion of rim 122 of proximal seal retaining portion 120. Proximal shelf 166 is configured to abut distal surface 123 of rim 122. Distal shelf 168 is configured to engage a distal surface 192 of seal 190.

Each finger of the plurality of fingers 128 is configured to engage one engagement aperture of the plurality of engagement apertures 170. More particularly, and with reference to FIG. 5, a body 129 of each finger 128 is configured to engage a first portion 172 of engagement aperture 170, and a lip 131 of each finger 128 is configured to engage a second portion 174 of engagement aperture 170. Moreover, each finger 128 is flexible such that lip 131 is able to move into and out of engagement with a wall 174a defining second portion 174 engagement aperture 170 to facilitate engagement between finger 128 and engagement aperture 170. Additionally, as can be appreciated, an angled surface 128a of finger 128 and an angled surface 172a adjacent first portion 172 of engagement aperture 170 also facilitate engagement between finger 128 and engagement aperture 170.

It is envisioned that each finger 128 and each engagement aperture 170 can be disengaged from one another by moving lip 131 radially inward with respect to engagement aperture 170. More particularly, it is envisioned that a tool can be inserted through second portion 174 of engagement aperture 170, into contact with lip 131 of finger 128 to move lip 131 radially inward of wall 174a, thus enabling proximal movement of proximal seal retaining portion 120 (at least the portion of which that is adjacent the finger 128 that has been disengaged from the respective engagement aperture 170) with respect to distal seal retaining portion 160.

While the illustrated embodiments illustrate a particular number of fingers 128 and engagement apertures 170, the present disclosure includes embodiments having more or fewer fingers 128 and/or engagement apertures 170 than the amount shown. Additionally, while the illustrated embodiments show an equal amount of fingers 128 and engagement apertures 170, it is envisioned that there are more engagement apertures 170 than fingers 128. For instance, it is envisioned that there are twice as many engagement apertures 170 than fingers 128. Such an embodiment enables proximal seal retaining portion 120 and distal seal retaining portion 160 to engage each other in twice as many rotational positions, which may be helpful if an engagement aperture 170 becomes damaged, for instance. Here, it is envisioned that distal seal retaining portion 160 includes a second C-shaped projection 181 (described in further detail below with regard to the embodiment shown in FIG. 16). Additionally, the circumferential spacing of fingers 128 and engagement apertures 170 may be different than the illustrated spacing.

Figure 14:
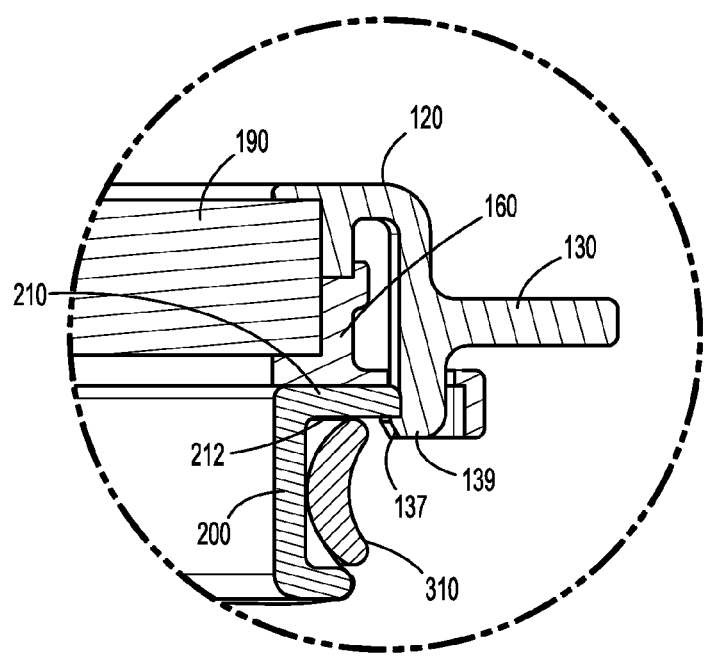
FIG. 14 is an enlarged view of the area of detail indicated in FIG. 13.
Figure 15:
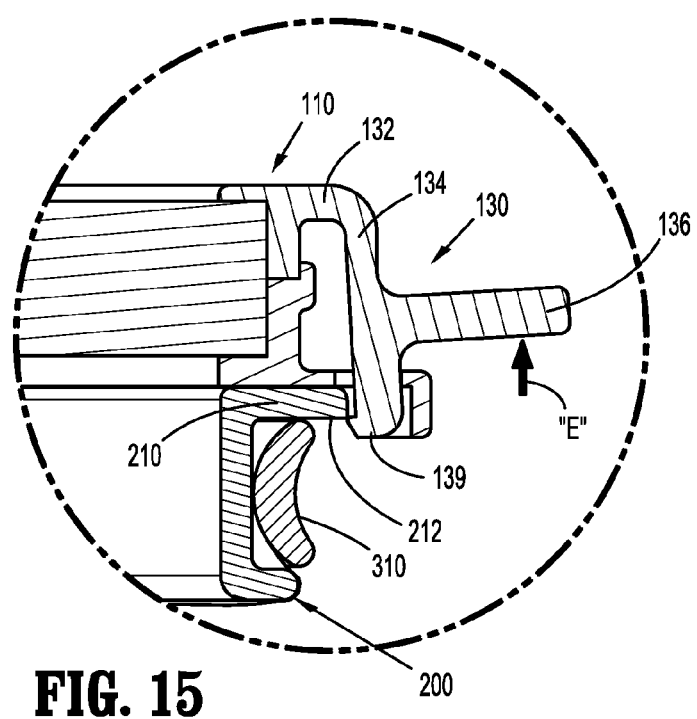
FIG. 15 is a similar view as FIG. 14, but illustrates a proximally-directed force being applied to a flexible tab of the access port assembly, and the resulting disengagement between the access port assembly and the ring.

With particular reference FIGS. 2, 14 and 15, outer ring 180 of distal seal retaining portion 160 includes a substantially C-shaped projection 181 extending radially outward therefrom. C-shaped projection 181 defines an opening 182 therein, which is configured to allow a portion of flexible tab 130 (e.g., engagement structure 139 and a distal portion of leg 134) to extend therethrough.

Referring now to FIGS. 3 and 6, lip 184 of distal seal retaining portion 160 is shown. In the illustrated embodiments, lip 184 extends radially inward from outer ring 180 in a location that is opposite (i.e., 180°) from C-shaped projection 181. As shown in FIG. 6, lip 184 is configured to engage a distal surface 212 of a proximal wall 210 of ring 200.

Figure 8B:
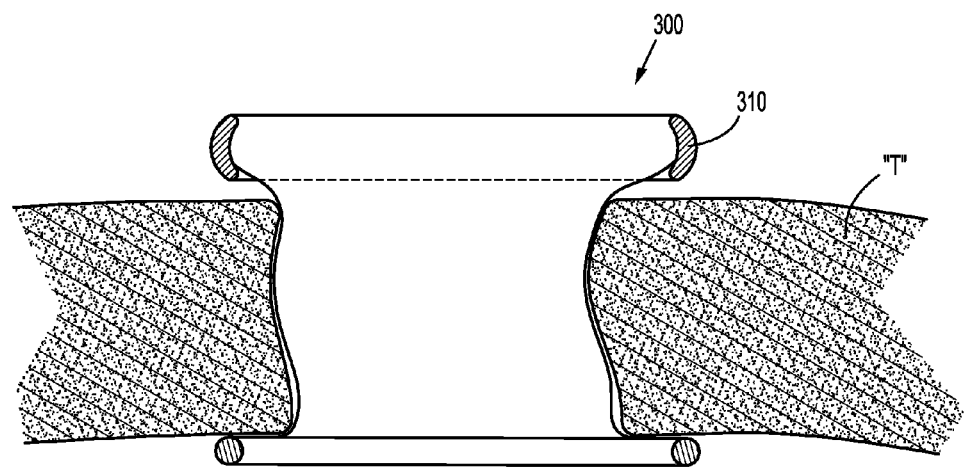
FIG. 8B is a cross-sectional view of the surgical access assembly of FIG. 7 installed in tissue and showing the proximal portion of the surgical access assembly in a convex orientation.
Figure 9:
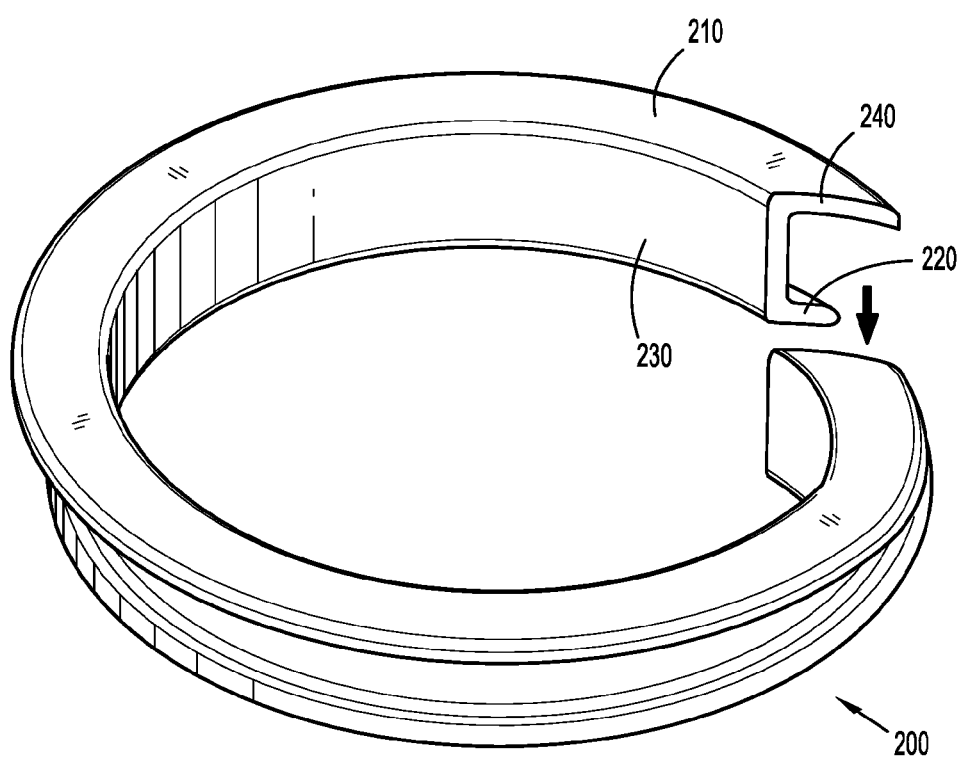
FIG. 9 is a perspective view of the ring of the surgical access attachment of FIGS. 1 and 2.

With particular reference to FIGS. 9-15, ring 200 is shown. Ring 200 includes proximal wall 210, a distal wall 220, and an intermediate wall 230 which interconnects proximal wall 210 and distal wall 220. As noted above, ring 200 is configured to mechanically engage proximal portion 310 of surgical access device 300. Moreover, ring 200 is configured mechanically engage proximal portion 310 of surgical access device 300 when proximal portion 310 is in a concave orientation (FIG. 8A) or when proximal portion 310 is in a convex orientation (FIG. 8B). Additionally, ring 200 includes a discontinuity 240 therein, which is configured to facilitate removable engagement between ring 200 and proximal portion 310 of surgical access device 300. When engaged with proximal portion 310 of surgical access device 300 (as shown in FIGS. 10-15), intermediate wall 230 of ring 200 is disposed radially inward of proximal portion 310 (e.g., a proximal lip) of surgical access device 300. Additionally, distal surface 212 of proximal wall 210 is positioned proximally of a proximal-most surface of surgical access device 300.

In use, and with reference to FIGS. 4-6, when proximal seal retaining portion 120 and distal seal retaining portion 160 are approximated, an inner surface 165 of proximal edge 164 engages an outer surface 125 of rim 122, proximal shelf 166 engages distal surface 123 of rim 122, and at least one finger of the plurality of fingers 128 mechanically engages an engagement aperture of the plurality of engagement apertures 170 to mechanically couple proximal seal retaining portion 120 and distal seal retaining portion 160.

Figure 10:
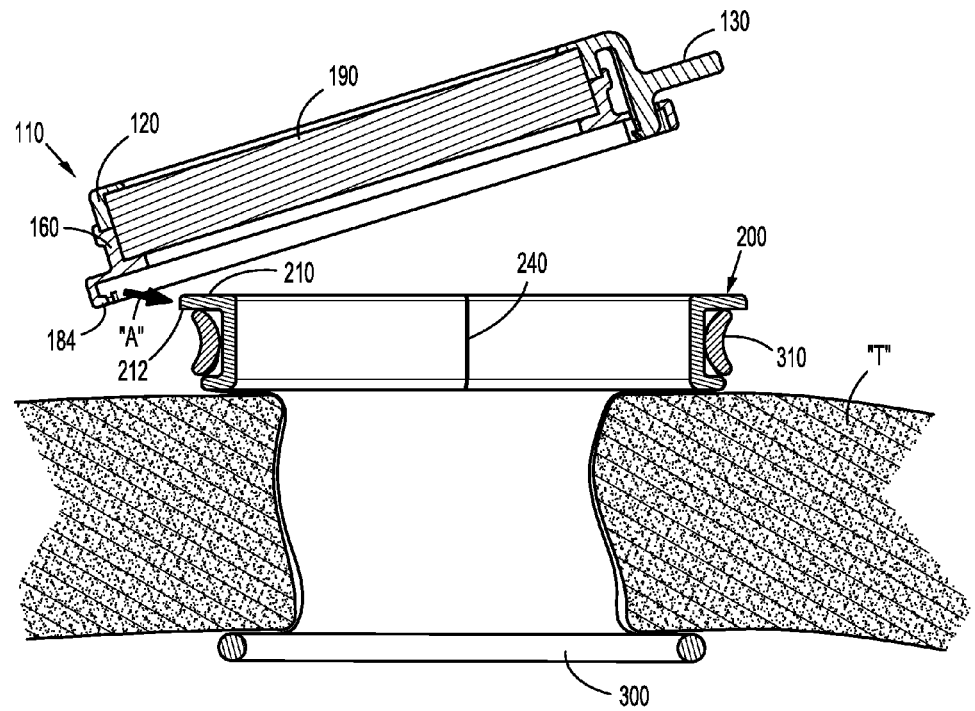
FIGS. 10-12 are cross-sectional views illustrating various steps of the engagement between the surgical access attachment of FIGS. 1-6 and 9 with the surgical access device of FIGS. 7-8B.
Figure 11:
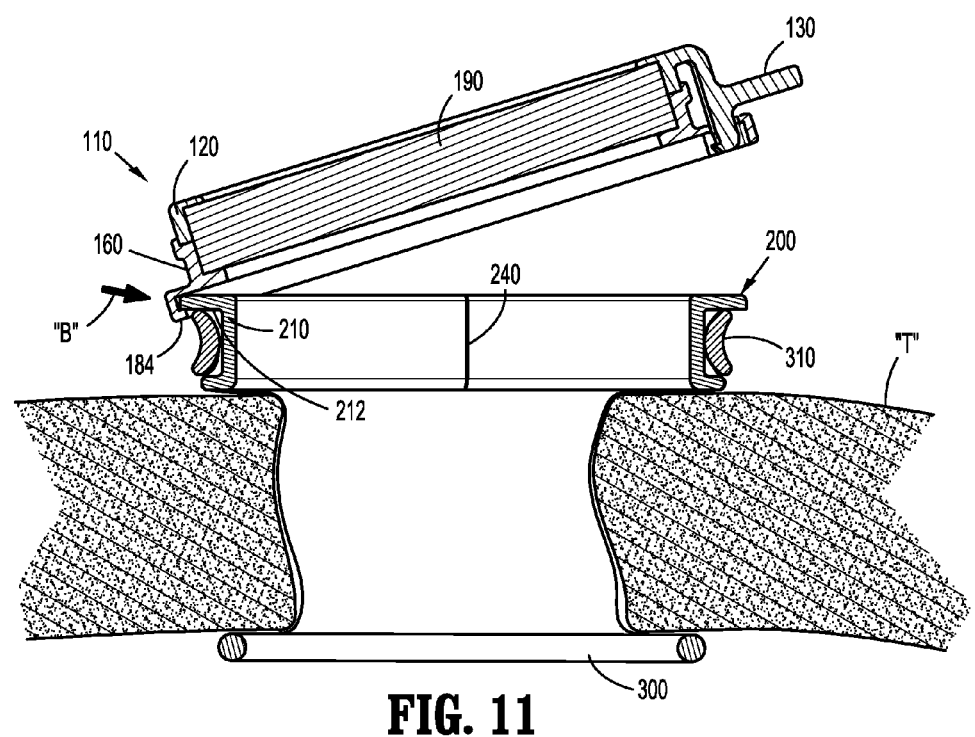
Figure 12:
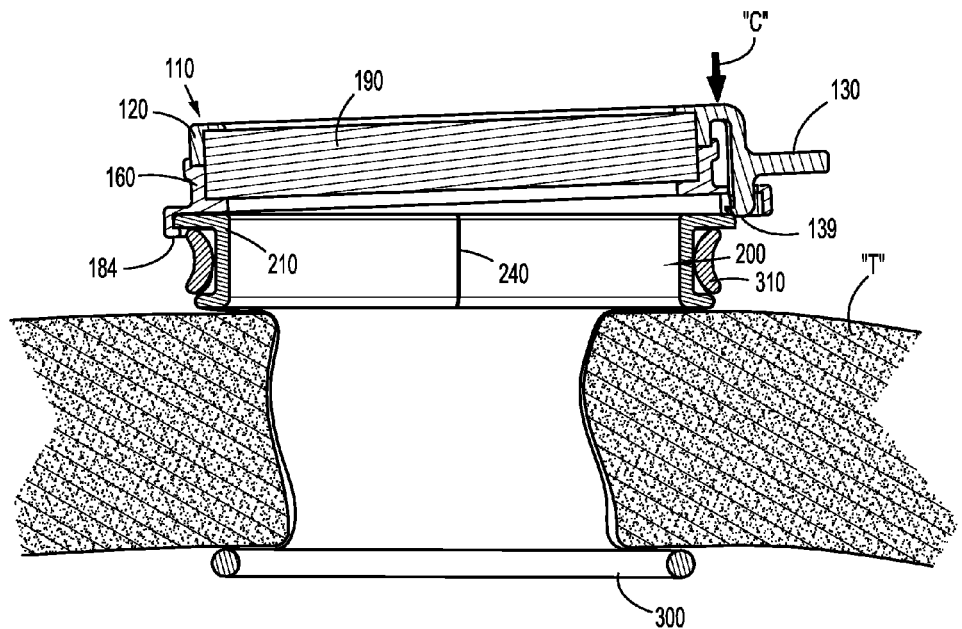

Additionally, and with reference to FIGS. 10-15, to mechanically engage access portion assembly 110 with ring 200 (e.g., after ring 200 is engaged with surgical access device 300), lip 184 of distal seal retaining portion 160 is moved into engagement with proximal wall 210 of ring 200 (e.g., lip 184 is moved distally of a distal surface 212 of proximal wall 210) (see arrows "A" and "B" in FIGS. 10 and 11). The opposite portion of access portion assembly 110 (e.g., the portion of access portion assembly 110 including flexible tab 130) is then moved generally distally (see arrows "C" and "D" in FIGS. 12 and 13), and such that engagement structure 139 of flexible tab 130 moves distally of proximal wall 210 of ring 200 (see FIGS. 13 and 14). With particular reference to FIG. 14, an angled surface 137 on engagement structure 139 of flexible tab 130 facilitates the radially outward movement of flexible tab 130 to enable engagement structure 139 to be properly positioned. It is envisioned that flexible tab 130 is biased radially inward such that engagement structure 139 thereof moves toward its biased position and into engagement with distal surface 212 of proximal wall 210 of ring 200 after access portion assembly 110 has been moved sufficiently distally with respect to ring 200. It is further envisioned that a user can exert a distal force upon engagement portion 136 in the general direction of arrows "C" and "D" in FIGS. 12 and 13 to help engagement structure 139 move radially inward and into engagement with distal surface 212 of proximal wall 210 of ring 200.

As can be appreciated the engagement between access portion assembly 110 and ring 200 can be accomplished single-handedly, thus allowing the clinician more freedom during, before, and after the surgical procedure, for example. More particularly, it is envisioned that a clinician can use a single handle to quickly and efficiently engage access portion assembly 110 and ring 200, without the need of rotating any components, for instance.

With particular reference to FIG. 15, to disengage access portion assembly 110 from ring 200, a user exerts a generally proximal force (see arrow "E" in FIG. 15) against engagement portion 136. A predetermined amount of force causes leg 134 of flexible tab 130 to flex a sufficient amount with respect to proximal portion 132, to cause engagement structure 139 to move radially outward and out of engagement with distal surface 212 of proximal wall 210 of ring 200, thereby permitting the portion of access portion assembly 110 including flexible tab 130 to move proximally with respect to ring 200 (e.g., in the direction opposite arrows "C" and "D" in FIGS. 12 and 13), which then allows lip 184 of distal seal retaining portion 160 to move out of engagement with proximal wall 210 of ring 200 (e.g., in the direction opposite arrows "A" and "B" in FIGS. 10 and 11), and allows complete disengagement between access portion assembly 110 and ring 200.

As can be appreciated the disengagement between access portion assembly 110 and ring 200 can be accomplished single-handedly, thus allowing the clinician more freedom during, before, and after the surgical procedure, for example. More particularly, it is envisioned that a clinician can use a single finger to press proximally or upward on flexible tab 130 to quickly accomplish this disengagement, without the need of rotating or unscrewing any components, for instance.

Figure 16:
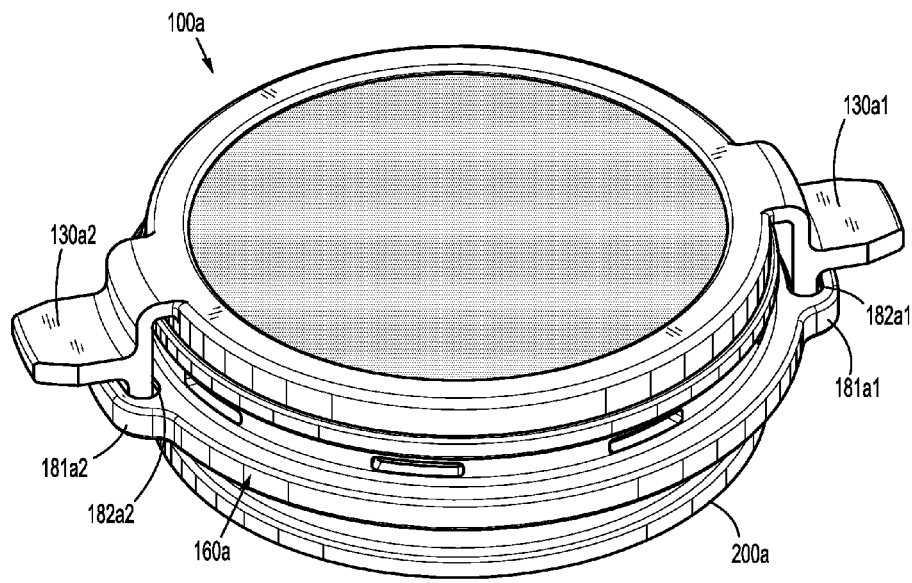
FIG. 16 is a perspective view of an alternate embodiment of a surgical access attachment which includes an access portion assembly having two flexible tabs.
Figure 17:
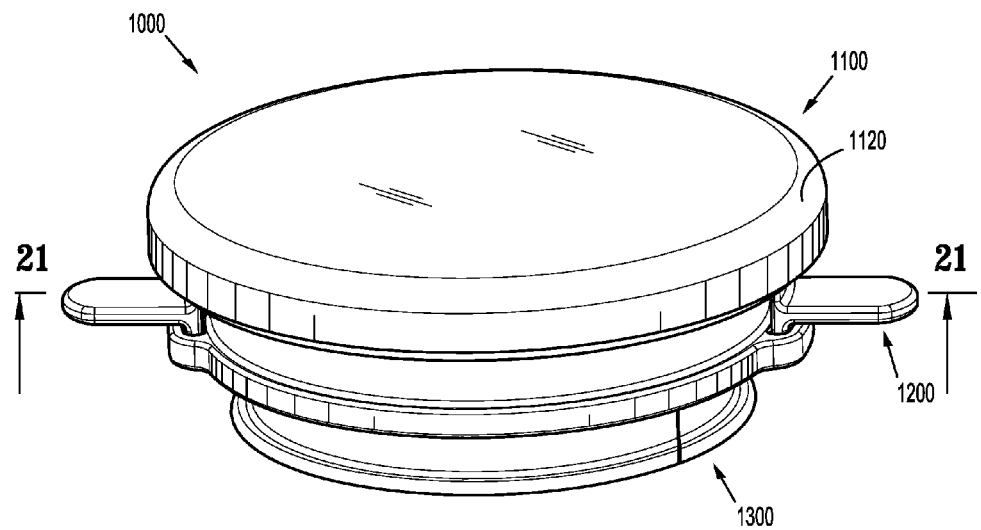
FIG. 17 is a perspective view of an additional alternate embodiment of a surgical access attachment.

Referring now to FIG. 16, another embodiment of surgical access attachment is shown and is referred to as reference character 100a. Surgical access attachment 100a is similar to surgical access attachment 100 of FIG. 1, but surgical access attachment 100a includes two flexible tabs $130a_1$ and $130a_2$. Here, second flexible tab $130a_2$, effectively replaces lip 184 of distal seal retaining portion 160 of surgical access attachment 100. More particularly, an engagement structure (not explicitly shown in FIG. 16; similar to engagement structure 139 of surgical access attachment 100) of second flexible tab $130a_2$ takes the place of lip 184. (See also FIG. 21, which illustrates a surgical access attachment 1000 including a pair of flexible tabs 1280) Additionally, a distal seal retaining portion 160a of surgical access attachment 100a includes first and second C-shaped projections $181a_1$ and $181a_2$, which each define a respective opening $182a_1$ and $182a_2$ therein.

Here, as can be appreciated, engagement and disengagement between access port assembly 110*a* and a ring 200*a* is accomplished similarly to engagement and disengagement between access port assembly 110 and ring 200, as discussed above.

Referring now to FIGS. 17-22 another embodiment of a surgical access attachment is shown and is referred to as reference character 1000. Surgical access attachment 1000 is configured for use with a surgical access device 300 (see FIGS. 7 and 8) for facilitating access to a surgical site. More particularly, surgical access attachment 1000, or portions thereof, are configured to be selectively removably attached to surgical access device 300, e.g., with the use of a single hand. That is, surgical access attachment 1000, or portions thereof, are configured to engage surgical access device 300 in a simple, one-handed manner, and surgical access attachment 1000, or portions thereof, are configured to disengage surgical access device 300 in a simple, one-handed manner.

Figure 18:
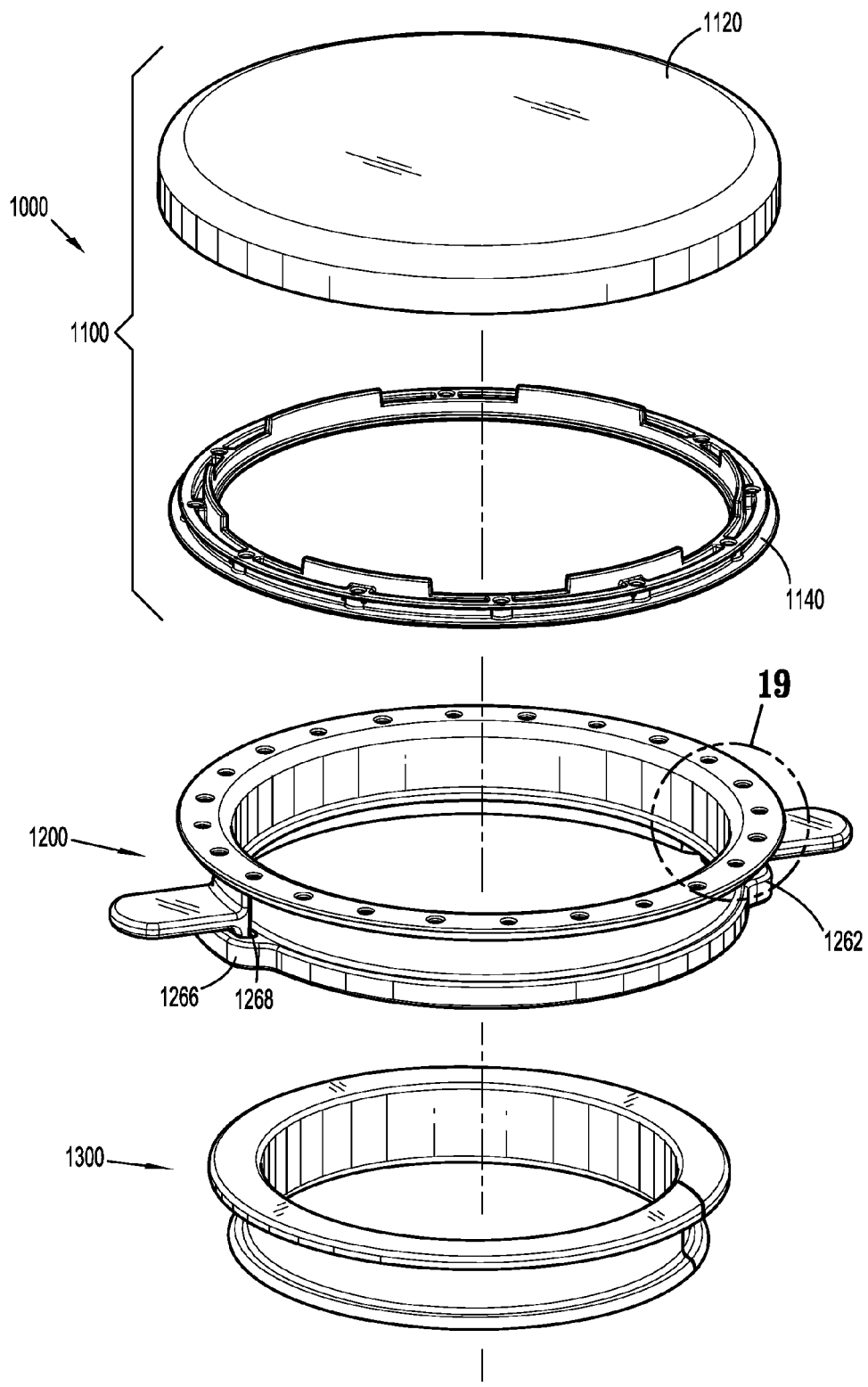
FIG. 18 is an assembly view of the surgical access attachment of FIG. 17, which includes an overmold assembly having a seal, a retaining assembly, and a ring.

With particular reference to FIG. 18, surgical access attachment 1000 includes a seal assembly 1100, a body portion 1200, and a ring 1300. Seal assembly 1100 includes a seal 1120 and a seal retaining member 1140, which are overmolded together. As discussed above with regard to seal 190, seal 1120 can be any suitable type of seal. Seal assembly 1100 is configured to mechanically engage body portion 1200, and body portion 1200 is configured to be selectively removably attached to ring 1300, as discussed in further detail below.

Figure 19:
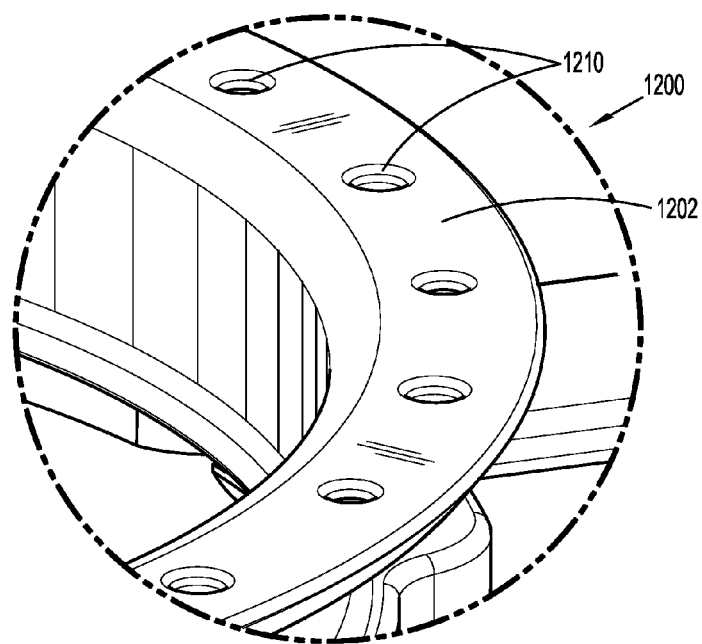
FIG. 19 is an enlarged view of a portion of the retaining assembly of FIG. 18.
Figure 20:
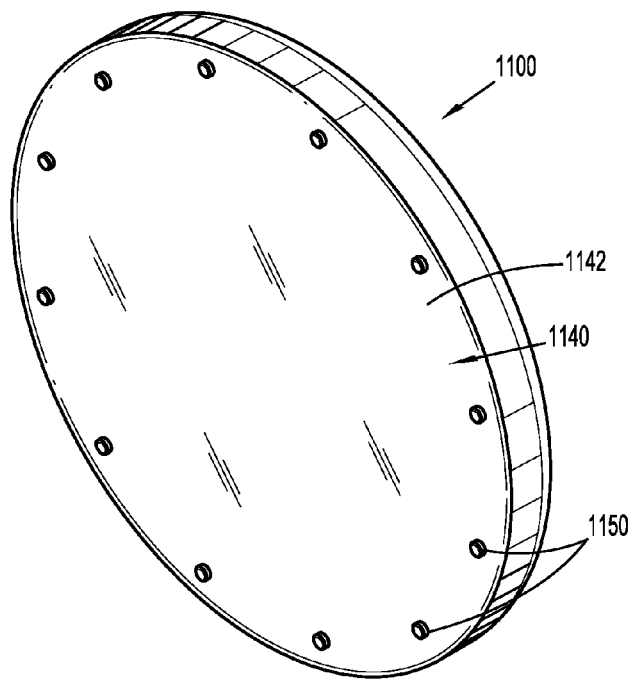
FIG. 20 is a perspective view illustrating a distal surface of the overmold assembly of the surgical access attachment of FIGS. 17-18.

With particular reference to FIGS. 19 and 20, the engagement between seal assembly 1100 and body portion 1200 is shown. A distal surface 1142 of seal retaining member 1140 includes a plurality of pins 1150 extending distally therefrom (FIG. 20), and a proximal surface 1202 of body portion 1200 includes a plurality of holes 1210 therein (FIG. 19). Each pin 1150 of seal retaining member 1140 is configured to frictionally engage one hole of the plurality of holes 1210 of body portion 1200 to secure (e.g., removably secure) seal assembly 1100 and body portion 1200. As can be appreciated, the number of holes of the plurality of holes 1210 helps determine the number of possible radial orientations of seal assembly 1100 with respect to body portion 1200. While the illustrated embodiment shows a certain number of pins 1150 and holes 1210, more or fewer pins 1150 and/or holes 1210 may be included. Additionally, body portion 1200 may include the same number of holes 1210 as there are pins 1150, or body portion 1200 may include more holes 1210 than pins 1150 without departing from the scope of the present disclosure. Further, the orientation and/or spacing of holes 1210 and pins 1150 may differ from the illustrated orientation and spacing.

Figure 21:
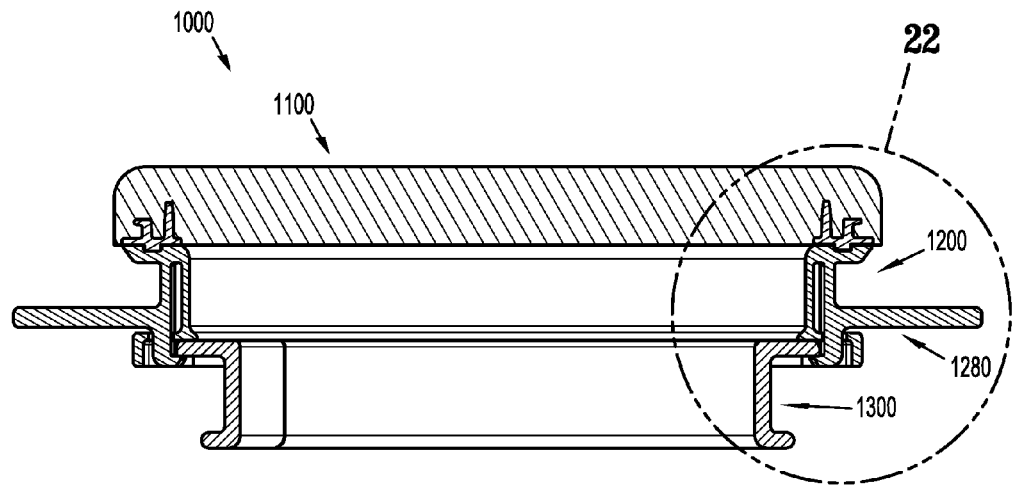
FIG. 21 is a cross-sectional view of the surgical access attachment of FIGS. 17-18 taken along line 21-21 of FIG. 17.
Figure 22:
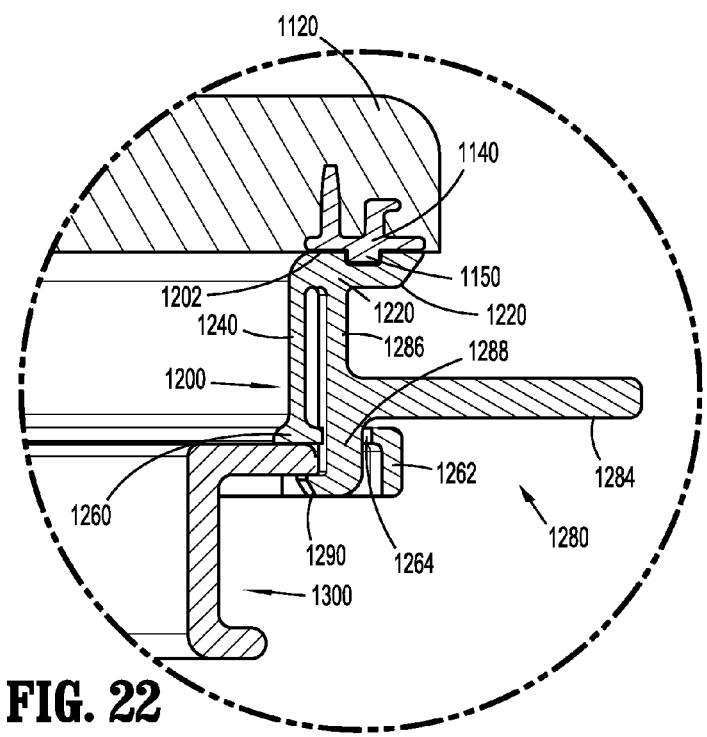
FIG. 22 in an enlarged view of the area of detail indicated in FIG. 21.

Referring now to FIGS. 21 and 22, the engagement between body portion 1200 and ring 1300 is shown. Body portion 1200 includes a proximal band 1220, an intermediate band 1240, a distal band 1260, and a pair of flexible tabs 1280. Proximal band 1220 includes proximal surface 1202 having plurality of holes 1210. Intermediate band 1240 interconnects proximal band 1220 and distal band 1260. Distal band 1260 includes a first C-shaped projection 1262 defining an opening 1264 therein, and a second C-shaped projection 1266 defining an opening 1268 therein (see FIGS. 18 and 22).

With continued reference to FIG. 22, each flexible tab 1280 depends distally from proximal band 1220, and includes a leg 1282, an engagement portion 1284, and a living hinge 1286. Living hinge 1286 interconnects leg 1282 and proximal band 1220, and enables leg 1282 to flex with respect to proximal band 1220. Engagement portion 1284 extends radially outward from leg 1282 and is configured for engagement by a user to facilitate the flexing of leg 1282 with respect to proximal band 1220 (e.g., to disengage body portion 1200 from ring 1300). A distal portion 1288 of leg 1282 of each flexible tab 1280 extends through opening 1264, 1268 of respective C-shaped projection 1262, 1266. Additionally, leg 1282 includes an engagement structure 1290 disposed on a distal end thereof, which is configured to mechanically engage a portion of ring 1300. Ring 1300 is similar to ring 200 of surgical access attachment 100, as discussed above.

Additional details of the removable attachment between body portion 1200 and ring 1300 are similar to those discussed above with regard to the removable attachment between access port assembly 110 and ring 200.

The present disclosure also relates to methods of using the devices described herein. For example, the present disclosure includes methods of single-handedly engaging and disengaging a surgical access attachment (including a seal assembly associated therein) with a surgical access device.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Persons skilled in the art will understand that the various apparatus, and corresponding methods of use described herein, and shown in the accompanying drawings, constitute non-limiting, exemplary embodiments of the present disclosure, and that additional components and features may be added to any of the embodiments discussed herein above without departing from the scope of the present disclosure.

Additionally, persons skilled in the art will understand that the elements and features shown or described in connection with one exemplary embodiment may be combined with those of another embodiment without departing from the scope of the present disclosure, and will appreciate further features and advantages of the presently disclosed subject matter based on the above-described embodiments and the claims. Accordingly, the present disclosure is not limited by what has been particularly shown and described.

Although the foregoing disclosure has been described in some detail by way of illustration and example, for purposes of clarity or understanding, it will be obvious that certain changes and modifications may be practiced within the scope of the appended claims.

What is claimed is:

1. A surgical access attachment for use with a surgical access device, the surgical access attachment comprising:
  a ring configured to engage a proximal portion of a surgical access device, the ring including a proximal wall, a distal wall, and an intermediate wall interconnecting the proximal wall and the distal wall; and
  an access portion assembly including a lip and a flexible tab having an engagement structure, the lip configured to selectively engage the ring, wherein the lip is disposed 180° from the flexible tab, each of the lip and the flexible tab is configured to engage a distal surface of the proximal wall of the ring, the engagement structure being configured to selectively engage the ring, the access portion assembly configured to retain a seal;

wherein the access portion assembly is configured to disengage from the ring in response to a predetermined amount of force exerted on the flexible tab.

2. The surgical access attachment according to claim 1, wherein the access portion assembly is configured to disengage from the ring in response to a predetermined amount of proximally-directed force exerted on the flexible tab.

3. The surgical access attachment according to claim 1 wherein the access portion assembly consists of two features that are configured to removably engage the ring, the two features including the flexible tab and the lip.

4. The surgical access attachment according to claim 1 wherein a distal-most portion of the flexible tab is co-planar with a distal-most portion of the lip.

5. The surgical access attachment according to claim 1, wherein the proximal wall of the ring is configured to be positioned proximally of a proximal-most portion of the surgical access device.

6. The surgical access attachment according to claim 1, wherein the access portion assembly includes a proximal seal retaining portion and a distal seal retaining portion.

7. The surgical access attachment according to claim 6, wherein the at least one flexible tab extends from the proximal seal retaining portion.

8. The surgical access attachment according to claim 6, wherein the lip is configured to selectively engage the ring, the flexible tab extends from the proximal seal retaining portion, and the lip extends from the distal seal retaining portion.

9. The surgical access attachment according to claim 6, wherein the flexible tab extends from the proximal seal retaining portion and at least partially through an opening of the distal seal retaining portion.

10. The surgical access attachment according to claim 9, wherein the opening of the distal seal retaining portion is defined by a C-shaped projection extending radially outward from an outer ring of the distal seal retaining portion.

11. The surgical access attachment according to claim 6, wherein the proximal seal retaining portion includes a plurality of fingers, and wherein the distal seal retaining portion includes a plurality of engagement apertures, each finger of the plurality of fingers is configured to mechanically engage one engagement aperture of the plurality of apertures.

12. The surgical access attachment according to claim 1, wherein the access portion assembly is configured to engage the ring in a single-handed manner.

13. The surgical access attachment according to claim 12, wherein the access portion assembly is configured to disengage the ring in a single-handed manner.

14. The surgical access attachment according to claim 1, wherein the access portion assembly is configured to non-rotatably engage the ring in a single-handed manner.

15. The surgical access attachment according to claim 14, wherein the access portion assembly is configured to non-rotatably disengage the ring in a single-handed manner.

16. A surgical access attachment for use with a surgical access device, the surgical access attachment comprising:
a ring configured to engage a proximal portion of a surgical access device; and
an access portion assembly including a proximal seal retaining portion, a distal seal retaining portion, a flexible tab having an engagement structure extending from the proximal seal retaining portion, and a lip extending from the distal seal retaining portion, the engagement structure being configured to selectively engage the ring, the access portion assembly configured to retain a seal, the lip being configured to selectively engage the ring;
wherein the access portion assembly is configured to disengage from the ring in response to a predetermined amount of force exerted on the flexible tab.

17. The surgical access attachment according to claim 14, further comprising a lip disposed 180° from a flexible tab of the flexible tab on the access portion assembly, the lip configured to selectively engage the ring.

18. A surgical access attachment for use with a surgical access device, the surgical access attachment comprising:
a ring configured to engage a proximal portion of a surgical access device; and
an access portion assembly including a proximal seal retaining portion, a distal seal retaining portion, a flexible tab having an engagement structure, the engagement structure configured to selectively engage the ring, the access portion assembly configured to retain a seal, the proximal seal retaining portion including a plurality of fingers, the distal seal retaining portion including a plurality of engagement apertures, each finger of the plurality of fingers is configured to mechanically engage one engagement aperture of the plurality of apertures;
wherein the access portion assembly is configured to disengage from the ring in response to a predetermined amount of force exerted on the flexible tab.

19. The surgical access attachment according to claim 18, further comprising a lip disposed 180° from the flexible tab on the access portion assembly, the lip configured to selectively engage the ring.

* * * * *